(12) United States Patent
Brunn et al.

(10) Patent No.: US 10,933,006 B2
(45) Date of Patent: Mar. 2, 2021

(54) AQUEOUS SURFACTANT COMPOSITIONS

(71) Applicant: BASF SE, Ludwigshafen am Rhein (DE)

(72) Inventors: Claudia Brunn, Düsseldorf-Holthausen (DE); Ansgar Behler, Düsseldorf-Holthausen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/301,472

(22) PCT Filed: May 11, 2017

(86) PCT No.: PCT/EP2017/061324
§ 371 (c)(1),
(2) Date: Nov. 14, 2018

(87) PCT Pub. No.: WO2017/198537
PCT Pub. Date: Nov. 23, 2017

(65) Prior Publication Data
US 2019/0216706 A1 Jul. 18, 2019

(30) Foreign Application Priority Data
May 18, 2016 (EP) .................................. 16170204

(51) Int. Cl.
| | | |
|---|---|---|
| *A61K 8/41* | (2006.01) | |
| *A61K 8/46* | (2006.01) | |
| *A61K 8/42* | (2006.01) | |
| *A61K 31/63* | (2006.01) | |
| *A61K 8/44* | (2006.01) | |
| *C11D 1/12* | (2006.01) | |
| *C11D 17/00* | (2006.01) | |
| *A61Q 19/00* | (2006.01) | |
| *A61Q 19/10* | (2006.01) | |
| *A61Q 5/02* | (2006.01) | |
| *C11D 1/37* | (2006.01) | |
| *C11D 3/04* | (2006.01) | |
| *A61Q 9/02* | (2006.01) | |
| *C11D 1/28* | (2006.01) | |
| *C11D 1/04* | (2006.01) | |
| *C11D 11/00* | (2006.01) | |

(52) U.S. Cl.
CPC .............. *A61K 8/466* (2013.01); *A61K 8/41* (2013.01); *A61K 8/463* (2013.01); *C11D 1/37* (2013.01); *C11D 3/046* (2013.01); *A61K 2800/596* (2013.01); *A61Q 5/02* (2013.01); *A61Q 9/02* (2013.01); *A61Q 19/10* (2013.01); *C11D 1/04* (2013.01); *C11D 1/123* (2013.01); *C11D 1/28* (2013.01); *C11D 11/0023* (2013.01)

(58) Field of Classification Search
CPC .... A01N 25/30; A01N 41/04; A01N 2300/00; A01N 33/12; A01N 41/02; A61K 8/416; A61K 8/35; A61K 8/42; A61K 9/0014; A61K 2800/596; A61K 8/463; A61K 47/14; A61Q 19/10; A61Q 5/02; A61Q 19/00
See application file for complete search history.

(56) References Cited

U.S. PATENT DOCUMENTS

| | | | |
|---|---|---|---|
| 2,195,088 A * | 3/1940 | Keppler | ................ C07C 309/07 562/109 |
| 5,925,603 A * | 7/1999 | D'Angelo | .............. A61K 8/442 510/119 |
| 6,172,026 B1 * | 1/2001 | Ospinal | .................... C11D 1/37 510/152 |

(Continued)

FOREIGN PATENT DOCUMENTS

| | | |
|---|---|---|
| DE | 4220580 A1 | 1/1994 |
| FR | 3013968 A1 | 6/2015 |

(Continued)

OTHER PUBLICATIONS

Anonymous, "Hair and Body Shampoo," GNPD, Mintel (Dec. 1, 2005), Database accession No. 3600935, XP002762134, "Ingredients."

(Continued)

*Primary Examiner* — Tracy Liu
(74) *Attorney, Agent, or Firm* — Marshall, Gerstein & Borun LLP

(57) ABSTRACT

Aqueous surfactant compositions comprising
  one or more alpha-sulfo fatty acid disalt (A) of general formula (I)

$$R^1CH(SO_3M^1)COOM^2 \quad (I),$$

in which the radical $R^1$ is a linear or branched alkyl or alkenyl radical having 6 to 18 carbon atoms and the radicals $M^1$ and $M^2$, independently of each other, are selected from H, Li, Na, K, Ca/2, Mg/2, ammonium, and alkanolamine,
  one or more sulfosuccinate (B) of general formula (II)

$$R^{31}-O-CO-CH(SO_3M^{16})-CH_2-COOM^{17} \quad (II)$$

wherein the radical $R^{31}$ is a linear or branched alkyl or alkenyl radical having 6 to 22 carbon atoms or an alkoxylated linear or branched alkyl or alkenyl radical having 6 to 22 carbon atoms and the radicals $M^{16}$ and $M^{17}$, independently of each other, are selected from the group comprising H, Li, Na, K, Ca/2, Mg/2, ammonium and alkanolamines, and
  water. The compositions have good foaming ability, good skin compatibility, and a pleasant sensory feel to the foam, and are suitable for cosmetic products detergents, and cleaners.

9 Claims, No Drawings

(56) References Cited

U.S. PATENT DOCUMENTS

2017/0283741 A1 10/2017 Behler et al.
2018/0119002 A1* 5/2018 Back .................. C09K 8/584

FOREIGN PATENT DOCUMENTS

WO      WO-98/44907 A1    10/1998
WO    WO-2016/030172 A1    3/2016

OTHER PUBLICATIONS

European Search Report for EP Patent Application No. 16170204.8, dated Oct. 10, 2016.
International Search Report for Patent Application No. PCT/EP2017/061324, dated Jun. 21, 2017.

* cited by examiner

AQUEOUS SURFACTANT COMPOSITIONS

CROSS-REFERENCE TO RELATED APPLICATIONS

This is a U.S. national phase of International Application No. PCT/EP2017/061324, filed May 11, 2017, which claims the benefit of European Patent Application No. 16170204.8, filed May 18, 2016.

FIELD OF THE INVENTION

The present invention relates to aqueous surfactant compositions with a content of alpha-sulfo fatty acid disalts and sulfosuccinates.

PRIOR ART

Anionic surfactants are some of the most widespread interface-active compounds and, apart from being used in detergents and cleaners, are also used for diverse purposes in the field of cosmetics. Customary anionic surfactants as are used in particular in cosmetics are the salts of alkyl ether sulfates (alkyl polyether sulfates, fatty alcohol polyglycol ether sulfates, in short also ether sulfates). They are characterized by a strong foaming ability, high cleaning power, low sensitivity to hardness and grease and are used widely for producing cosmetic products such as, for example, hair shampoos, foam or shower baths, but also in hand dishwashing detergents.

For many current applications, apart from a good interface-active effect, further requirements are placed on anionic surfactants. A high dermatological compatibility is required in particular in cosmetics. In addition, good foaming ability and a pleasant sensory feel to the foam is generally desired. Furthermore, there is a need for anionic surfactants which can be produced at least partially from biogenic sources and specifically also renewable raw materials.

DESCRIPTION OF THE INVENTION

The object of the present invention was to provide aqueous surfactant compositions which are characterized by the properties specified below:
good foaming ability.
pleasant sensory feel to the foam.
good skin compatibility.
The invention firstly provides aqueous surfactant compositions comprising
one or more alpha-sulfo fatty acid disalts (A) of general formula (I), $$R^1CH(SO_3M^1)COOM^2 \quad (I),$$

in which the radical $R^1$ is a linear or branched alkyl or alkenyl radical having 6 to 18 carbon atoms and the radicals $M^1$ and $M^2$—independently of each other—are selected from the group comprising H, Li, Na, K, Ca/2, Mg/2, ammonium and alkanolamines,
one or more sulfosuccinates (B) of general formula (II), $$R^{31}\text{—O—CO—CH}(SO_3M^{16})\text{—}CH_2\text{—}COOM^{17} \quad (II),$$

wherein the radical $R^{31}$ is a linear or branched alkyl or alkenyl radical having 6 to 22 carbon atoms or an alkoxylated linear or branched alkyl or alkenyl radical having 6 to 22 carbon atoms and the radicals $M^{16}$ and $M^{17}$—independently of each other—are selected from the group comprising H, Li, Na, K, Ca/2, Mg/2, ammonium and alkanolamines,
water,
where the following proviso applies:
if the aqueous surfactant composition one or more ester sulfonates (E) of general formula (V), $$R^2CH(SO_3M^7)COOR^3 \quad (V)$$

in which the radical $R^2$ is a linear or branched alkyl or alkenyl radical having 6 to 18 carbon atoms and the radical $R^3$ is a linear or branched alkyl or alkenyl radical having 1 to 20 carbon atoms, where the radical $R^3$ can logically be an alkenyl radical or be branched only above 3 carbon atoms, and the radical $M^7$ is selected from the group comprising Li, Na, K, Ca/2, Mg/2, ammonium and alkanolamines, it is the case that the compounds (A)—based on the totality of the compounds (A) and (E)—must be present to an extent of 50% by weight or more—and in particular to an extent of 90% by weight or more.

The aqueous surfactant compositions according to the invention are characterized by the following advantageous properties:
Good foaming ability and pleasant sensory feel to the foam. In this regard, it may be noted that particularly in the field of cosmetics, foaming ability can be understood to mean different aspects, for example it being possible to use any of foam volume, foam stability, foam elasticity, water content of the foam as well as optical features of the foam such as, for example, the pore size, for the purposes of assessing the foam. The compositions according to the invention have a large foam volume during the foaming. In practice, the initial foaming takes place within a relatively short period (from a few seconds to one minute). Typically, during initial foaming, a shower gel or a shampoo is spread and caused to foam by rubbing between hands, skin and/or hair. In the laboratory, the foaming behavior of an aqueous surfactant solution can be assessed e.g. by agitating the solution within a comparatively short time period by means of stirring, shaking, pumping, bubbling through a gas stream or in other way. Subjective assessment of the foam sensory feel can be made by test subjects. For this purpose, aspects such as creaminess, elasticity, moldability of the foam may be assessed.
Good skin and mucosa compatibility. These can be detected by in vitro methods known to those skilled in the art (e.g. RBC or HET-CAM) and also by test subjects (e.g. patch test).
Outstanding care performance on skin and hair. This can be assessed, for example in test subjects by reference to subjective skin feel (smoothness, dryness etc.) or haptics and feel of the treated hair. Mechanical measurement methods, such as combability of the hair, can also be used.
Good storage stability. This is then the case if the aqueous compositions do not exhibit any visible (e.g. cloudiness, discoloration, phase separation) or measurable (e.g. pH, viscosity, active substance content) changes.
Good applicability and processability. The compositions can be dissolved rapidly and without supply of heat on introducing in water.
Good clear solubility and transparency. The aqueous surfactant compositions do not have a tendency to precipitation or cloudiness.
Sufficiently high viscosity, which is understood in the context of the present invention to mean a value of 1000 mPas or higher (measured with a Brookfield RV laboratory rheometer at 23° C., 12 rpm, spindle set RV 02 to 07 (spindle choice depending on viscosity range)). As is known, "mPas" means millipascal seconds.

Good cleaning performance. The aqueous surfactant compositions are suitable for removing and emulsifying soiling, especially fat or oil-containing soiling, from solid or textile surfaces.

The compounds (A)

The compounds (A), which are referred to within the context of the present invention as alpha-sulfo fatty acid disalts, are obligatory for the aqueous surfactant compositions according to the invention. They have the formula (I) specified above $$R^1CH(SO_3M^1)COOM^2 \qquad (I),$$

in which the radical $R^1$ is a linear or branched alkyl or alkenyl radical having 6 to 18 carbon atoms and the radicals $M^1$ and $M^2$—independently of each other—are selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In one embodiment, the proviso applies that the proportion of the compounds (A) in the aqueous surfactant compositions in which the radical $R^1$ is an alkenyl radical—based on the total amount of the compounds (A)—is 3% by weight or less.

In a preferred embodiment, the radical $R^1$ in the formula (I) is a saturated, linear alkyl radical having 10 to 16 carbon atoms, where, with regard to the compounds (A) it is the case that the proportion of the compounds (A) in which the radical $R^1$ is a decyl and/or a dodecyl radical—based on the total amount of the compounds (A)—is 70% by weight or more and preferably 90% by weight or more.

Preferably, the radicals $M^1$ and $M^2$ in formula (I) are selected from the group comprising H (hydrogen) and Na (sodium).

The compounds (A) can be prepared by all methods known appropriately to the person skilled in the art. A particularly preferred method of preparation here is the sulfation of the corresponding carboxylic acids. Here, the corresponding carboxylic acid and in particular the corresponding fatty acids are reacted with gaseous sulfur trioxide, the sulfur trioxide being used preferably in an amount such that the molar ratio of $SO_3$ to fatty acid is in the range from 1.0:1 to 1.1:1. The crude products obtained in this way, which are acidic sulfation products, are then partially or completely neutralized, preference being given to complete neutralization with aqueous NaOH. If desired, it is also possible to undertake purification steps and/or a bleaching (for adjusting the desired pale color of the products).

In a particularly preferred embodiment, the compounds (A) are used in technical-grade form. This means that the corresponding carboxylic acids, in particular native fatty acid, are sulfated with gaseous sulfur trioxide, as a result of which, following partial or complete neutralization of the resulting acidic sulfation products, a mixture of the compounds (A), (C) and (D) results. By virtue of corresponding adjustments of the reaction parameters (in particular molar ratio of carboxylic acid and sulfur trioxide, and also reaction temperature) it is possible to control the ratio of the compounds (A), (C) and (D). The compounds (C) and (D) are described below in the chapter "Preferred embodiments".

In the context of the present invention, preference is given to those technical-grade mixtures of alpha-sulfo fatty acid disalts which have the following composition:

the content of (A) is in the range from 60 to 100% by weight,
the content of (C) is in the range from 0 to 20% by weight,
the content of (D) is in the range from 0 to 20% by weight,
with the proviso that the sum of the components (A), (C) and (D) in this mixture is 100% by weight.

The Compounds (B)

The compounds (B), which in the context of the present invention are referred to as sulfosuccinates, are obligatory for the aqueous surfactant compositions according to the invention. They have the formula (II) specified above $$R^{31}-O-CO-CH(SO_3M^{16})-CH_2-COOM^{17} \qquad (II)$$

wherein the radical $R^{31}$ is a linear or branched alkyl or alkenyl radical having 6 to 22 carbon atoms or an alkoxylated linear or branched alkyl or alkenyl radical having 6 to 22 carbon atoms and the radicals $M^{16}$ and $M^{17}$—independently of each other—are selected from the group comprising H, Li, Na, K, Ca/2, Mg/2, ammonium and alkanolamines.

The compounds (B) can be prepared by all relevant methods known to those skilled in the art. An important approach to the compounds (B) is the following: in a two-stage process, maleic anhydride is initially esterified with an alcohol or an alcohol alkoxylate, which is to be understood as an addition product of ethylene oxide to an alcohol. The maleic ester obtained in this case is subsequently sulfonated in aqueous sodium hydrogensulfite solution.

In one embodiment, the proviso applies that the proportion of the compounds (B) in the aqueous surfactant compounds in which the radical $R^{31}$ is an alkenyl radical,—based on the total amount of the compounds (B)—is 3% by weight or less.

In one embodiment, the radical $R^{31}$ in formula (II) is a saturated, linear alkyl radical having 12 to 18 carbon atoms, wherein with respect to the compounds (B) it is the case that the proportion of the compounds (B) in which the radical $R^{31}$ is a dodecyl and/or a tetradecyl radical,—based on the total amount of the compounds (B)—is 70% by weight or more and preferably 90% by weight or more.

In one embodiment, the radical $R^{31}$ in formula (II) is a linear alkyl radical having 8 to 18 and especially 12 to 18 carbon atoms.

In a further preferred embodiment, the radical $R^{31}$ in formula (II) is a $-(CH_2-CH_2-O)_p-R^5$ group, where p is a number in the range from 1 to 4 and the radical $R^5$ is a linear alkyl radical having 12 to 18 carbon atoms.

Particular preference is given to compounds (B) with the INCI name Disodium Laureth Sulfosuccinate and Disodium Lauryl Sulfosuccinate.

The radicals $M^{16}$ and $M^{17}$ in formula (II) are preferably selected from the group comprising H (hydrogen) and Na (sodium).

PREFERRED EMBODIMENTS

In one embodiment, the aqueous surfactant compositions according to the invention comprise, besides the compounds (A), (B) and water, additionally one or more compounds (C) of general formula (III)

$$R^4COOM^5 \qquad (III)$$

In the formula (III), the radical $R^4$ is a linear or branched alkyl or alkenyl radical with 7 to 19 carbon atoms and the radical $M^5$ is selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In one embodiment, the aqueous surfactant compositions according to the invention comprise, besides the compounds (A), (B) and water, additionally one or more inorganic salts of sulfuric acid (D) of general formula (IV)

$$(M^6)_2SO_4 \quad (IV)$$

wherein $M^6$ is selected from the group comprising Li, Na, K, Ca/2, Mg/2, ammonium and alkanolamine. In this connection, particularly preferred alkanolamines are monoethanolamine, diethanolamine, triethanolamine and monoisopropanolamine.

In a preferred embodiment, the aqueous surfactant compositions according to the invention comprise the compounds (A), (B), (C) and (D). In this case, it is particularly preferable if the radicals $M^1$ and $M^2$ of the compounds (A), the radicals $M^{16}$ and $M^{17}$ of the compounds (B), the radical $M^5$ of the compounds (C) and the radical $M^6$ of the compounds (D) are selected from the group comprising H (hydrogen) and Na (sodium).

In one embodiment, the aqueous surfactant compositions according to the invention, in addition to the compounds (A), (B) and water, additionally comprise one or more compounds (F) of general formula (VI).

$$R^6CH_2-CO-CHR^7(SO_3M^8) \quad (VI),$$

in which the radicals $R^6$ and $R^7$—independently of each other—are a linear or branched alkyl radical having 6 to 18 carbon atoms and the radical M is selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In the context of the present invention, the compounds (F) are referred to as monosulfoketones.

In a preferred embodiment, the radicals $R^6$ and $R^7$ in the formula (VI)—independently of each other—are a saturated, linear radical having 10 to 16 carbon atoms, where, with regard to the compounds (F) it is the case that the proportion of the compounds (F) in which the radicals $R^6$ and $R^7$ are a decyl and/or a dodecyl radical—based on the total amount of the compounds (F)—is 70% by weight or more and preferably 90% by weight or more. Preferably, the radical $M^8$ in formula (VI) is selected from the group comprising H and Na.

In one embodiment, the aqueous surfactant compositions according to the invention, in addition to the compounds (A), (B) and water, additionally comprise one or more compounds (G) of general formula (VII)

$$(SO_3M^9)R^8CH-CO-CHR^9(SO_3M^{10}) \quad (VII),$$

in which the radicals $R^8$ and $R^9$—independently of each other—are a linear or branched alkyl radical having 6 to 18 carbon atoms and the radicals $M^9$ and $M^{10}$—independently of each other—are selected from the group comprising H, Li, Na, K, Ca/2, Mg/2, ammonium and alkanolamines. In this connection, particularly preferred alkanolamines are monoethanolamine, diethanolamine, triethanolamine and monoisopropanolamine.

In the context of the present invention, the compounds (G) are referred to as disulfoketones.

In a preferred embodiment, the radicals $R^8$ and $R^9$ in the formula (VII)—independently of each other—are a saturated, linear radical having 10 to 16 carbon atoms, where, with regard to the compounds (G) it is the case that the proportion of the compounds (G) in which the radicals $R^8$ and $R^9$ are a decyl and/or a dodecyl radical—based on the total amount of the compounds (G)—is 70% by weight or more and preferably 90% by weight or more. Preferably, the radicals $M^9$ and $M^{10}$ in formula (VII) are selected from the group comprising H and Na.

The preparation of the compounds (F) and (G) is not subject to any particular restrictions and they can be prepared by all methods known to those skilled in the art.

In one embodiment, the compounds (F) and (G) are prepared by sulfonation of the corresponding ketones with gaseous sulfur trioxide, as described in the German published specification DE-A-42,20,580.

In another embodiment, the preparation of the compounds (F) and (G) starts from fatty acids. In this case, the sulfation of liquid fatty acids with gaseous sulfur trioxide is conducted such that, in addition to disalts (A), the compounds (F) and (G) are also formed, which can be accomplished as a result of carrying out the sulfation as follows: the ratio of fatty acid raw materials, which may also be used in the form of mixtures of fatty acids of different chain length, and sulfur trioxide is adjusted so that 1.0 to 1.5 mol and especially 1.0 to 1.25 mol of $SO_3$ are used per mole of fatty acid(s). The fatty acids are introduced into the reactor at a reservoir temperature in the range of 70 to 100° C. After the sulfation, the resulting liquid sulfation product is maintained and aged at this temperature for 5 to 20 minutes in a temperature-controlled post-reaction coil. Neutralization is then effected with an aqueous base, preferably sodium hydroxide, generally in a pH range of 5 to 10, especially 5 to 7. Subsequently, an acidic bleaching—the pH here is adjusted to a value of 7 or less—may be carried out with hydrogen peroxide.

In one embodiment, the aqueous surfactant compositions according to the invention comprise the compounds (A), (B) and (F). It is particularly preferred in this case if the radicals $M^1$ and $M^2$ of the compounds (A) and the radicals $M^{16}$ and $M^{17}$ of the compounds (B) are selected from the group comprising H (hydrogen) and Na (sodium). The proviso applies in this case that the amount of the compounds (A) must be greater than the amount of the compounds (F).

In one embodiment, the aqueous surfactant compositions according to the invention comprise the compounds (A), (B) and (G). It is particularly preferred in this case if the radicals $M^1$ and $M^2$ of the compounds (A) and the radicals $M^{16}$ and $M^{17}$ of the compounds (B) are selected from the group comprising H and Na. The proviso applies in this case that the amount of the compounds (A) must be greater than the amount of the compounds (G)

In one embodiment, the aqueous surfactant compositions according to the invention comprise the compounds (A), (B), (F) and (G). It is particularly preferred in this case if the radicals $M^1$ and $M^2$ of the compounds (A) and the radicals $M^{16}$ and $M^{17}$ of the compounds (B) are selected from the group comprising H and Na. The proviso applies in this case that the amount of the compounds (A) must be greater than the sum of the amount of the compounds (F) and (G).

In one embodiment, the aqueous surfactant compositions according to the invention comprise the compounds (A), (B), (C), (D) and (F). It is particularly preferred in this case if the radicals $M^1$ and $M^2$ of the compounds (A), the radicals $M^{16}$ and $M^{17}$ of the compounds (B), the radical $M^5$ of the compounds (C) and the radical $M^6$ of the compounds (D) are selected from the group comprising H and Na. The proviso applies in this case that the amount of the compounds (A) must be greater than the amount of the compounds (F).

In one embodiment, the aqueous surfactant compositions according to the invention comprise the compounds (A), (B), (C), (D) and (G). It is particularly preferred in this case if the radicals $M^1$ and $M^2$ of the compounds (A), the radicals $M^{16}$ and $M^{17}$ of the compounds (B), the radical $M^5$ of the compounds (C) and the radical $M^6$ of the compounds (D) are selected from the group comprising H and Na. The proviso applies in this case that the amount of the compounds (A) must be greater than the amount of the compounds (G).

In one embodiment, the aqueous surfactant compositions according to the invention comprise the compounds (A), (B), (C), (D), (F) and (G). It is particularly preferred in this case if the radicals $M^1$ and $M^2$ of the compounds (A), the radicals $M^{16}$ and $M^{17}$ of the compounds (B), the radical $M^5$ of the compounds (C) and the radical $M^6$ of the compounds (D) are selected from the group comprising H and Na. The proviso applies in this case that the amount of the compounds (A) must be greater than the sum of the amount of the compounds (F) and (G).

If desired, the aqueous surfactant compositions according to the invention can additionally comprise one or more further surfactants which, in structural terms, do not belong to the aforementioned compounds (A), (B), (D), (E), (F) or (G). These surfactants may be anionic, cationic, nonionic or amphoteric surfactants.

Use of the Compositions

A further subject matter of the invention is the use of the aforementioned compositions for cosmetic products, and also detergents and cleaners.

With regard to cosmetic products, particular preference is given here especially to those which are present in the form of hair shampoos, shower gels, soaps, syndets, washing pastes, washing lotions, scrub preparations, foam baths, oil baths, shower baths, shaving foams, shaving lotions, shaving creams and dental care products (for example toothpastes, mouthwashes and the like).

With regard to cleaners, of preference here are in particular products with a low pH for cleaning hard surfaces, such as bath and toilet cleaners and the like, and also for cleaning and/or fragrance gels for use in sanitary installations.

EXAMPLES

Substances Used

DM water=demineralized water

SFA: alpha-sulfo fatty acid disalt of technical grade quality based on virgin $C_{12/14}$-fatty acid; composition: 74% by weight disodium 2-sulfolaurate, 13% by weight sodium laurate, 11% by weight sodium sulfate, 2% by weight water. The designation "laurate" in this case signifies that the $C_{12/14}$ weight ratio of the mixture of the virgin fatty acids on which they are based is 70:30.

SB3: Texapon SB3, Disodium Laureth Sulfosuccinate (INCI name), 33% by weight active substance, commercial product of BASF PCN Measurement and Test Methods Determination of the Foaming Capacity:

To test the foaming behaviour (rotor foam method), a commercial measuring instrument was used (Sita Foam Tester R-2000). Firstly an aqueous surfactant solution was prepared as follows: 1 g of active substance of each sample to be tested (as samples, SFA or SB3 or mixtures of these substances were used, see below; in the case of SFA—as stated above—the active substance content is understood to mean the disalt content) was dissolved in 1 litre of DM water at 20° C. The pH of the solution was adjusted to 5.5 with citric acid. The solution thus prepared was temperature-controlled at 30° C.

Measurement: From the temperature-controlled stock, 250 ml were transferred to the measuring instrument and foamed at a rotation speed of 1300 revolutions per minute for 10 seconds, the foam volume (in ml) present determined, then foamed for a further 10 seconds, the foam volume (in ml) present determined, and so on, i.e. every 10 seconds during foaming the foam height was determined. After a foaming time of 80 seconds, the measurement was terminated. The measurement was repeated 3 times on each sample, each with fresh solution from the same batch and the result of the measurements after 80 seconds stated as the average of these three measurements (see Table).

EXAMPLES

E1=Example 1 (Inventive)

A mixture of SFA and Texapon SB3 was used in which the ratio by weight of the respective active substance of SFA and SB3 was set at a value of 2:1. The experiment was carried out as described above under "Determination of the foaming capacity". The experimental data can be found in Table 1.

E2=Example 2 (Inventive)

A mixture of SFA and Texapon SB3 was used in which the ratio by weight of the respective active substance of SFA and SB3 was set at a value of 1:1.

E3=Example 3 (Inventive)

A mixture of SFA and Texapon SB3 was used in which the ratio by weight of the respective active substance of SFA and SB3 was set at a value of 1:2.

E4=Example 4 (Inventive)

A mixture of SFA and Texapon SB3 was used in which the ratio by weight of the respective active substance of SFA and SB3 was set at a value of 1:5.

C1=Comparative Example 1

Exclusively SFA was used.

C2=Comparative Example 2

Exclusively SB3 was used.

TABLE 1

Determination of the foaming capacity

| | E1 | E2 | E3 | E4 | C1 | C2 |
|---|---|---|---|---|---|---|
| Ratio SFA:SB3 | 2:1 | 1:1 | 1:2 | 1:5 | 1:0 | 0:1 |
| Foam volume after 80 seconds | 808 ml | 858 ml | 845 ml | 844 ml | 454 ml | 865 ml |

SFA alone shows an unsatisfactory foam volume (comparative example 1), whereas all mixtures of SFA with SB3 (surprisingly even example 1 with a significant excess of SFA) have a very high foam volume, comparable with that of SB3.

The invention claimed is:

1. An aqueous surfactant composition comprising
one or more alpha-sulfo fatty acid disalt (A) of general formula (I)

$$R^1CH(SO_3M^1)COOM^2 \qquad (I),$$

in which the radical $R^1$ is a saturated, linear alkyl radical having 10 to 16 carbon atoms and the radicals $M^1$ and $M^2$, independently of each other, are selected from the group consisting of H, Li, Na, K, Ca/2, Mg/2, ammonium, and alkanolamine, where with regard to the disalt (A), a proportion of the disalt (A) in which the radical $R^1$ is a decyl or a dodecyl radical, based on the total amount of the disalt (A), is 90% by weight or more,
one or more (B) sulfosuccinate
selected from the group consisting of disodium laureth sulfosuccinate and disodium lauryl sulfosuccinate, and,
water,
where the following provisos apply:
a ratio of disalt (A) to sulfosuccinate (B) is 2:1 to 1:2, by weight, and if the aqueous surfactant composition comprises one or more ester sulfonate (E) of general formula (V)

$$R^2CH(SO_3M^7)COOR^3 \qquad (V),$$

in which the radical $R^2$ is a linear or branched alkyl radical having 6 to 18 carbon atoms and the radical $R^3$ is a linear or branched alkyl radical having 1 to 20 carbon atoms, where the radical $R^3$ can be branched only above 3 carbon atoms, and the radical $M^7$ is selected from the group consisting of Li, Na, K, Ca/2, Mg/2, ammonium, and alkanolamine, it is the case that the disalt (A), based on the totality of the disalt (A) and the ester sulfonate (E), must be present to an extent of 90% by weight or more.

2. The composition according to claim 1, wherein the radicals $M^1$ and $M^2$ are selected from H (hydrogen) and Na (sodium).

3. The composition according to claim 1, wherein the composition additionally comprises one or more compound (C) of general formula (III)

$$R^4COOM^5 \qquad (III),$$

in which the radical $R^4$ is a linear or branched alkyl radical having 7 to 19 carbon atoms and the radical $M^5$ is selected from the group consisting of H, Li, Na, K, Ca/2, Mg/2, ammonium and alkanolamine.

4. The composition according to claim 1, wherein the composition additionally comprises one or more inorganic salt of sulfuric acid (D) of general formula (IV)

$$(M^6)_2SO_4 \qquad (IV),$$

wherein $M^6$ is selected from the group consisting of Li, Na, K, Ca/2, Mg/2, ammonium, and alkanolamine.

5. The composition according to claim 1, wherein the composition additionally comprises one or more monosulfoketone (F) of general formula (VI)

$$R^6CH_2-CO-CHR^7(SO_3M^8) \qquad (VI),$$

in which the radicals $R^6$ and $R^7$, independently of each other, are a linear or branched alkyl radical having 6 to 18 carbon atoms and the radical $M^5$ is selected from the group consisting of H, Li, Na, K, Ca/2, Mg/2, ammonium, and alkanolamine.

6. The composition according to claim 1, wherein the composition additionally comprises one or more disulfoketone (G) of general formula (VII)

$$(SO_3M^9)R^8CH-CO-CHR^9(SO_3M^{10}) \qquad (VII),$$

in which the radicals $R^8$ and $R^9$, independently of each other, are a linear or branched alkyl radical having 6 to 18 carbon atoms and the radicals $M^9$ and $M^{10}$, independently of each other, are selected from the group consisting of H, Li, Na, K, Ca/2, Mg/2, ammonium, and alkanolamine.

7. The composition according to claim 1 for use in cosmetic products, detergents, and cleaners.

8. The composition according to claim 1 for use in cosmetic products in the form of hair shampoos, shower gels, soaps, syndets, washing pastes, washing lotions, scrub preparations, foam baths, oil baths, shower baths, shaving foams, shaving lotions, shaving creams, and dental care products.

9. The composition according to claim 1 for use in products for cleaning hard surfaces.

* * * * *

UNITED STATES PATENT AND TRADEMARK OFFICE
CERTIFICATE OF CORRECTION

PATENT NO. : 10,933,006 B2
APPLICATION NO. : 16/301472
DATED : March 2, 2021
INVENTOR(S) : Claudia Brunn et al.

It is certified that error appears in the above-identified patent and that said Letters Patent is hereby corrected as shown below:

In the Claims

At Column 10, Lines 18, "$M^5$" should be -- $M^8$ --.

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*